(12) United States Patent
Dyba et al.

(10) Patent No.: US 9,720,221 B2
(45) Date of Patent: Aug. 1, 2017

(54) DEVICE AND METHOD FOR ACQUIRING A MICROSCOPIC IMAGE OF A SAMPLE STRUCTURE

(75) Inventors: Marcus Dyba, Heidelberg (DE); Jonas Foelling, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 361 days.

(21) Appl. No.: 13/812,443

(22) PCT Filed: Jul. 22, 2011

(86) PCT No.: PCT/EP2011/062605
§ 371 (c)(1),
(2), (4) Date: Jan. 25, 2013

(87) PCT Pub. No.: WO2012/013586
PCT Pub. Date: Feb. 2, 2012

(65) Prior Publication Data
US 2013/0128025 A1    May 23, 2013

(30) Foreign Application Priority Data

Jul. 28, 2010  (DE) ........................ 10 2010 036 709

(51) Int. Cl.
*H04N 5/253*   (2006.01)
*G02B 21/36*   (2006.01)
(Continued)

(52) U.S. Cl.
CPC ....... *G02B 21/365* (2013.01); *G01N 21/6458* (2013.01); *G02B 21/16* (2013.01);
(Continued)

(58) Field of Classification Search
CPC  G02B 21/365; G02B 21/367; G02B 21/6458; G02B 21/16; G02B 21/245; G02B 27/58; H04N 7/18; H04N 5/253
(Continued)

(56) References Cited

U.S. PATENT DOCUMENTS

2004/0113043 A1   6/2004  Ishikawa et al.
2005/0068614 A1   3/2005  Yoneyama et al.
(Continued)

FOREIGN PATENT DOCUMENTS

AT       402 863 B      9/1997
DE    101 00 246 A1     7/2002
(Continued)

OTHER PUBLICATIONS

International Preliminary Report on Patentability (PCT/IB/338 & PCT/IB/373) dated Feb. 7, 2013 (eight (8) pages).
(Continued)

*Primary Examiner* — Michael Lee
(74) *Attorney, Agent, or Firm* — Crowell & Moring LLP

(57) ABSTRACT

A device and a method for acquiring a microscopic image of a sample structure are described. An optic for imaging the sample structure and a reference structure is provided, as well as a drift sensing unit for sensing a drift of the sample structure relative to the optic on the basis of the imaged reference structure. The optic comprises a first sharpness plane for imaging the sample structure and at the same time a second sharpness plane, modifiable in location relative to the first sharpness plane, for imaging the reference structure.

6 Claims, 5 Drawing Sheets

(51) Int. Cl.
*G01N 21/64* (2006.01)
*G02B 21/16* (2006.01)
*G02B 21/24* (2006.01)
*G02B 27/58* (2006.01)

(52) U.S. Cl.
CPC ......... *G02B 21/245* (2013.01); *G02B 21/367* (2013.01); *G02B 27/58* (2013.01); *H04N 5/253* (2013.01)

(58) Field of Classification Search
USPC ........................................................ 348/79
See application file for complete search history.

(56) References Cited

U.S. PATENT DOCUMENTS

| | | | |
|---|---|---|---|
| 2005/0078361 | A1 | 4/2005 | Bewersdorf et al. |
| 2007/0122143 | A1 | 5/2007 | Okamoto |
| 2008/0182336 | A1 | 7/2008 | Zhuang et al. |
| 2009/0134342 | A1 | 5/2009 | Hell et al. |
| 2009/0195688 | A1* | 8/2009 | Henderson et al. .......... 348/345 |
| 2011/0160083 | A1 | 6/2011 | Hell et al. |
| 2012/0194903 | A1 | 8/2012 | Nishikawa |

FOREIGN PATENT DOCUMENTS

| | | |
|---|---|---|
| DE | 10 2006 021 317 B3 | 10/2007 |
| DE | 10 2008 024 568 A1 | 12/2009 |
| EP | 2 196 836 A1 | 6/2010 |
| JP | 2004-70276 A | 3/2004 |
| JP | 2005-107302 A | 4/2005 |
| JP | 2007-148221 A | 6/2007 |
| JP | 2010-139757 A | 6/2010 |
| WO | WO 00/68667 A1 | 11/2000 |
| WO | WO 2006/127692 A2 | 11/2006 |
| WO | WO 2007/128434 A1 | 11/2007 |
| WO | WO 2009/031477 A1 | 3/2009 |
| WO | WO 2009/085218 A1 | 7/2009 |
| WO | WO 2010/060515 A1 | 6/2010 |
| WO | WO 2011/007768 A1 | 1/2011 |

OTHER PUBLICATIONS

Written Opinion (PCT/ISA/237) dated Jan. 29, 2013 (eight (8) pages).
International Search Report with English translation dated Oct. 25, 2011 (seven (7) sheets).
German-language Written Opinion (PCT/ISA/237) (eight (8) sheets).
German Office Action dated Jul. 29, 2011 (four (4) sheets).
Rust et al., "Sub-diffraction-limit imaging by stochastic optical reconstruction microscopy (STORM)", Nature Methods, 2006, vol. 3, pp. 1-3 (three (3) sheets).
Geisler et al., "Resolution of $\lambda/10$ in fluorescence microscopy using fast single molecule photo-switching", Applied Physics A., 2007, vol. 88, pp. 223-226 (four (4) sheets).
Japanese Office Action dated May 12, 2015 with partial English-language translation (eleven (11) pages).
Japanese Office Action dated May 10, 2016 with English-language translation (4 pages).

* cited by examiner

DEVICE AND METHOD FOR ACQUIRING A MICROSCOPIC IMAGE OF A SAMPLE STRUCTURE

The invention relates to a method and a device for acquiring a microscopic image of a sample structure.

In the recent past, light-microscopy imaging methods have been developed with which, based on a sequential, stochastic localization of individual markers (in particular, fluorescent molecules), it is possible to display sample structures that are smaller than the diffraction-related resolution limit of classic light microscopes. Such methods are described, for example, in WO 2006/127692 A2; DE 10 2006 021 317 B3; WO 2007/128434 A1, US 2009/0134342 A1; DE 10 2008 024 568 A1; "Sub-diffraction-limit imaging by stochastic optical reconstruction microscopy (STORM)," Nature Methods 3, 793-796 (2006), M. J. Rust, M. Bates, X. Zhuang; "Resolution of Lambda/10 in fluorescence microscopy using fast single molecule photo-switching," Geisler C. et al., Appl. Phys. A, 88, 223-226 (2007). This new branch of microscopy is also referred to as "localization microscopy." The methods applied are known in the literature, for example, under the designations PALM, FPALM, (F)STORM, PALMIRA, or GSDIM.

The new methods have in common the fact that the sample structures to be imaged are prepared with markers that possess two distinguishable states, namely a "bright" state and a "dark" state. For example, if fluorescent dyes are used as a marker, the bright state is then a fluorescence-capable state and the dark state is a non-fluorescence-capable state. In order for sample structures to be imaged at a resolution that is smaller than the classic resolution limit of the image-producing optic, a small subset of the markers is then repeatedly prepared into the bright state. This subset is referred to hereinafter as an "active subset." The active subset must be selected so that the average spacing between adjacent markers in the bright state—and thus the state capable of imaging by light microscopy—is greater than the resolution limit of the imaging optical system. The luminance signals of the active subset are imaged onto a spatially resolving light detector, e.g. a CCD camera. A light distribution in the form of a spot of light, whose size is determined by the resolution limit of the image-producing optical system, is therefore acquired from each marker.

The result is that a plurality of individual raw-data images are acquired, in each of which a different active subset is imaged. In an image analysis process, the center points of the light distributions (representing the markers that are in the bright state) are then determined in each individual raw-data image. The center points of the light distributions identified from the individual raw-data images are then combined into one overall depiction in the form of an overall-image data set. The high-resolution overall image produced by this overall depiction reflects the distribution of the markers. "Raw data" are thus understood hereinafter as data that have not yet been subjected to the image analysis process in order to determine the center point positions.

For a representative reproduction of the sample structure to be imaged, a sufficiently large number of signals must be detected. But because the number of markers in the particular active subset is limited by the minimum average spacing that must exist between two markers in the bright state, a very large number of individual raw-data images must be acquired in order to image the sample structure completely. The number of individual raw-data images is typically in a range from 10,000 to 100,000.

The time required for acquiring an individual raw-data image is limited at the low end by the maximum image acquisition rate of the light detector. This leads to comparatively long total acquisition times for a sequence of individual raw-data images that is necessary for the overall depiction. The total acquisition time can thus amount to as much as several hours.

Motion of the sample being imaged, relative to the image-producing optical system, can occur over this long total acquisition time. Because all the individual raw-data images must be combined after center-point determination in order to create a high-resolution overall image, any relative motion between the sample and the image-producing optic that occurs during the acquisition of two successive individual raw-data images degrades the spatial resolution of the overall image. In many cases this relative motion derives from a systematic mechanical motion of the system (also referred to as "mechanical drift") that is caused, for example, by thermal expansion or contraction, by mechanical stresses, or by a change in the consistency of lubricants that are used in the mechanical components.

The problems described above will be illustrated below with reference to FIGS. 1 to 3.

FIG. 1a schematically depicts a sample structure 2 that is made up of three concentric circular rings. It will be assumed in what follows that the structural features of this sample structure 2 that are to be imaged, in particular the spacings of the concentric circular rings from one another, are so small that they are below the diffraction-limited resolution limit of light-microscopy imaging.

When sample structure 2 shown in FIG. 1a is then provided with markers, and when these markers are brought into the bright state (in which they can thereby be imaged by light microscopy), what results because of the diffraction-limited resolution capability of light-microscopy imaging is a microscope image of the kind shown in FIG. 1b, in which the individual circular rings of sample structure 2 that are provided with markers are no longer distinguishable. In FIG. 1b (and also in FIGS. 2 and 3), sample structure 2 shown in FIG. 1a is indicated by dashed circular lines in order to illustrate the situation. As shown in FIG. 1b, the result here is a blurred and therefore spatially unresolved light distribution 4, indicated by hatching.

FIG. 2a shows a sequence of individual raw-data images, in each of which an active subset of markers is imaged. The active markers appear in the individual raw-data images as extended spots of light 6 whose size is determined by the resolution limit of the image-producing optic. As FIG. 2a shows, spots of light 6 are each at an average spacing from one another which is greater than this resolution limit that determines the size of spots of light 6.

FIG. 2b illustrates the manner in which center point positions 8 of spots of light 6 are identified, in the image analysis process mentioned above, from the individual raw-data images. Center point positions 8 determined from the individual raw-data images are then combined into an overall depiction shown in FIG. 2c. The overall depiction in 2c thus supplies a high-resolution overall image of sample structure 2 shown in FIG. 1a.

FIGS. 3a and 3b illustrate how a degradation of the spatial resolution of the overall image can occur as a consequence of a relative motion that takes place, during the acquisition of two successive individual raw-data images, between sample structure 2 being imaged and the image-producing optical system. In this example, serving solely for illustration, the center point positions determined from a first individual raw-data image are assumed to be depicted by circles 10, and the center point positions determined from a second individual raw-data image immediately following it by squares 12.

FIG. 3a shows the ideal situation with no mechanical drift. Center point positions 10 and 12 identified from the two individual raw-data images precisely reproduce sample structure 2 shown in FIG. 1a. FIG. 3b depicts the case in which mechanical drift causes a displacement of the second individual raw-data image with respect to the first individual raw-data image. Center point positions 12 derived from the second individual raw-data image are correspondingly offset with respect to center point positions 10 derived from the first individual raw-data image. The result of this is a degradation in the spatial resolution of the overall image.

A variety of methods for sensing and compensating for drift of the sample structure relative to the imaging optic are known. For example, it is proposed to mark the sample structure with reference markers, for example gold microspheres or fluorescent nanoparticles, and to optically sense their position simultaneously with actual acquisition of an image of the sample structure. It is usual in this context to optically sense the sample structure in a first wavelength region (i.e. in the wavelength region of the fluorescent light, in the case of a fluorescence microscope), and the reference structure in a second wavelength region different therefrom (for example, in the wavelength region of the illumination light, when reflective gold microspheres are used). Two separate light detectors, or a single light detector operating with two color channels, can be used for this. The drift can then be determined from the drift-related positional displacements of the acquired images of the reference structure.

In the method recited above, the reference markers are introduced into the sample at a comparatively high concentration. This is the only way to ensure that reference markers are present in sufficient quantity, in the sharpness plane of the imaging optic into which the sample structure is introduced, to be imaged sharply by the optic onto the light detector. The reference markers that are present at a high concentration, and constitute foreign bodies, have a disadvantageous effect especially in the context of light-microscopy imaging of living cell structures. The sample preparation that must be performed in order to introduce the reference markers is moreover comparatively complex.

It is also possible to sense the mechanical drift using suitable sensors, e.g. capacitive distance measuring devices. Such sensors are usually attached to the sample holder on which the sample is mounted. It is disadvantageous in this context that the drift of the sample holder determined via the sensor does not necessarily correspond to the actual drift of the sample structure if any relative motion between the sample holder and sample cannot be ruled out. The use of such sensors is moreover technically comparatively complex.

The object of the invention is to describe a device and a method for acquiring a microscopic image of a sample structure that enable reliable sensing, with little technical complexity, of a drift of the sample structure relative to the imaging optic.

The invention achieves this object as recited in the claims.

The invention provides, for the imaging optic, two sharpness planes or focal planes physically separated from one another and shiftable with respect to one another, of which the first serves for imaging of the sample structure and the second for imaging of the reference structure. The term "plane" is of course to be understood here not as a plane in the strictly mathematical sense, i.e. a strictly two-dimensional geometric space, but rather as that region within the object space of the optic within which the object (in this case the sample structure or reference structure, respectively) is imaged sharply onto the image plane, and which is usually characterized by the depth of focus of the optic.

Assuming a fixed first sharpness plane of the optic, into which the sample structure to be imaged is brought, for example, by means of a focusing drive attached to a sample holder, the optic according to the present invention then makes it possible to adjust the second sharpness plane as desired onto a suitable reference structure. In particular, the reference structure does not need to be located in the immediate physical vicinity of the first sharpness plane in which the sample structure is arranged. This makes it possible to use any desired structure that has a fixed spatial relationship to the imaging [sic] sample structure as a reference structure for drift sensing. Possibilities are, for example, structures imageable by light microscopy that are already present in the sample or even on the sample holder. The reference structure can in particular be embodied on a coverslip that is usually used to immobilize the sample of a carrier of the sample holder. Alternatively, the reference structure can be embodied on, for example imprinted into, the carrier itself.

Autofluorescent structures in the sample can likewise be used for drift sensing. The markers used in localization microscopy, which, as mentioned earlier, have a bright and a dark state, can also constitute the reference structure. It is thus possible, for example, to generate the reference structure by bringing all the markers out of the dark state into the bright state. The drift can then be determined on the basis of the structure thereby generated, which because of the limited resolution capability of the optic is not suitable for imaging the sample structure.

The fact that in the context of the device according to the present invention, the second sharpness plane of the optic can be adjusted as desired relative to the first sharpness plane makes it easy always to find a suitable reference structure and use it to sense the drift. This is advantageous in particular when reference markers constituting foreign bodies, for example gold microspheres, are introduced into the sample. By displacing the second sharpness plane of the optic it is easy to find a sample region in which enough reference markers are present. The result is that the concentration of reference markers that need to be introduced into the sample is decreased, which is advantageous especially when imaging living cell structures. This furthermore simplifies sample preparation.

Optical sensing of drift according to the present invention, using the imaging optic itself, is associated with less technical complexity than is the case with the use of the external sensors known from the existing art. If structures present in the sample itself are used as reference structures, the drift of the sample structure can then be sensed more reliably and more precisely than is possible with the external sensors recited above. With the latter, for example, there is not always assurance that the drift measured at the sensor in fact corresponds to the drift of the sample structure. This is true in particular when thermal expansion occurs on the sample holder on which the sensors are usually attached.

The optic preferably comprises an objective for imaging the sample structure, and a sub-optic that coacts with the objective in order to image the reference structure and is adjustable in order to modify the location of the second sharpness plane. In this embodiment the objective therefore contributes both to imaging of the sample structure and to imaging of the reference structure, while the sub-optic is used only to image the reference structure, and serves to adjust the second sharpness plane relative to the first sharpness plane.

In a preferred refinement, the sub-optic encompasses at least two lenses movable relative to one another. By shifting these lenses with respect to one another, the focal length of the optical system constituted by the sub-optic and the objective, and thus the second sharpness plane, can easily be adjusted.

Alternatively, it is also possible to provide the sub-optic as a stationary, i.e. non-shiftable, optic, and to embody the light detector, onto which the reference structure is imaged by the sub-optic, movably along the optical axis. In this case, displacement of the light detector, and thus of the imaging plane, also shifts the sharpness region of the sub-optic, i.e. the second sharpness plane.

The sub-optic is preferably arranged in a secondary beam path that is diverted from a main beam path intended for imaging of the sample structure. Arrangement of the sub-optic in a secondary beam path makes possible simple and reliable adjustment of the second sharpness plane without thereby influencing the imaging of the sample structure.

A further preferred embodiment provides for a first light detector, arranged in the main beam path, onto which the sample structure is imageable, and for a second light detector, arranged in the secondary beam path, onto which the reference structure is imageable. The two light detectors can be used, for example, to image the sample structure using light in a first wavelength region, and the reference structure using light in a second wavelength region different therefrom. If the device according to the present invention is used in fluorescence microscopy, the first light detector then receives the fluorescent light emitted from the sample structure, while the second light detector receives, for example, the excitation light which is reflected at the reference structure and with which the sample structure is excited to emit the fluorescent light.

It is likewise possible, however, to provide only a single light detector that is designed for separate sensing of light in different wavelength regions. This has the advantage that the sample structure and the reference structure are imaged in one and the same light path, thereby eliminating drift effects that can occur between different light paths.

If a main beam path and a secondary beam path are provided, the device then preferably comprises a light-separating optical element with which the secondary beam path is diverted from the main beam path and directed onto the second light detector. This light-separating optical element is, for example, a dichroic mirror if the sample structure is imaged in a first wavelength region and the reference structure in a second wavelength region different therefrom. If the two structures are imaged in one and the same wavelength region, the light-separating optical element is then, for example, a semitransparent mirror.

In a particularly preferred embodiment, an autofocus apparatus is provided in order to adjust the second sharpness plane onto the reference structure. An autofocus apparatus of this kind ensures that the optic remains focused on the reference structure if, for example, the sample is shifted in the sample depth direction by means of a focusing drive engaging on the sample holder, in order to bring a sample structure of interest into the first sharpness plane. The effect of an autofocus apparatus of this kind is thus that the second sharpness plane, which is adjusted e.g. onto a reference structure embodied on the coverslip of the sample holder, is automatically tracked upon displacement of the sample. It is possible to use as an autofocus apparatus both a passive apparatus, which functions e.g. with the illumination light reflected at the reference structure, and an active apparatus that comprises a separate light source for illuminating the reference structure.

The drift of the sample structure relative to the optic, sensed by way of the reference structure, can be used to correct the acquired individual images after the fact on the basis of the drift that has been identified. It is likewise possible, however, to compensate for drift already during imaging of the sample structure. This can be done, for example by providing a positioning member to which control can be applied, via a drift signal generated by the drift sensing unit, in order to move at least a portion of the optic and/or of the sample holder for drift compensation. This configuration can be embodied in the manner of a control loop, in which a continuous reference/actual comparison is implemented and the aforesaid portion of the optic or of the sample holder is driven with reference to drift signal on the basis of that comparison.

Particularly precise drift compensation is obtained when an individual image of the reference structure is also acquired for each individual image of the sample structure, and the drift is sensed for each individual image. It is also possible, however, to acquire an image of the reference structure, and determine the drift, only at longer predetermined time intervals. This applies both for the case in which image compensation is performed after the fact on the acquired individual images, and for the case in which drift compensation is accomplished during measurement, i.e. during imaging of the sample structure, by way of a positioning member. In the former case, if the individual images are drift-corrected after the fact and if the drift is sensed not for each individual image but instead only for each n-th individual image (n being a natural number greater than 1), the drift for the images located therebetween can then be determined by interpolation.

A light source that illuminates the sample structure and at the same time the reference structure through the objective is preferably provided. In this embodiment the sample structure and the reference structure are illuminated using incident light microscopy. In an alternative embodiment only the sample structure is illuminated using the incident light method, but the reference structure is illuminated using the transmitted light method. In this case a separate light source is provided for illuminating the reference structure. The wavelength of the illumination light emitted from this light source can be selected appropriately as a function of the reference structure being used.

The device according to the present invention is profitably usable with all items of equipment which make possible a magnified depiction of a sample structure, and in which drift sensing and drift compensation is desired in order to increase imaging accuracy. Utilization as a fluorescence microscope that operates according to one of the methods grouped together earlier under the term "localization microscopy" is particularly preferred.

The invention will be explained in further detail below with reference to the Figures, in which:

FIG. 1a schematically depicts an exemplifying sample structure whose structural features to be imaged by light microscopy are smaller than the resolution limit of light-microscopy imaging;

Figure 1A:
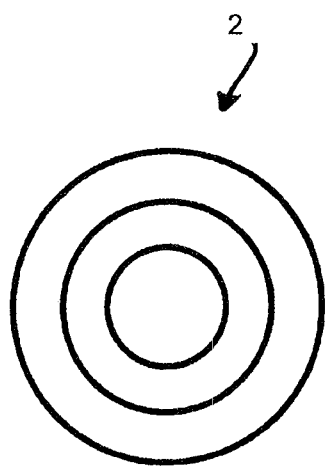
FIG. 1b is a schematic depiction showing a resolution-limited light-microscopy image of the sample structure according to FIG. 1a prepared with markers.
Figure 1B:
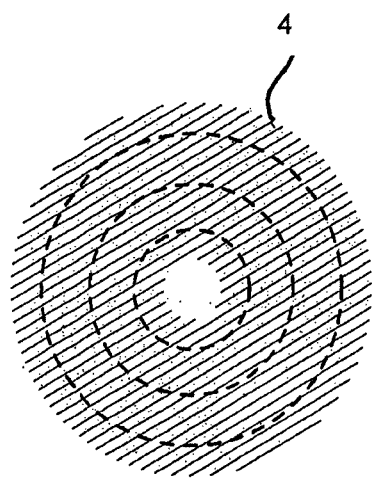
Figure 2A:
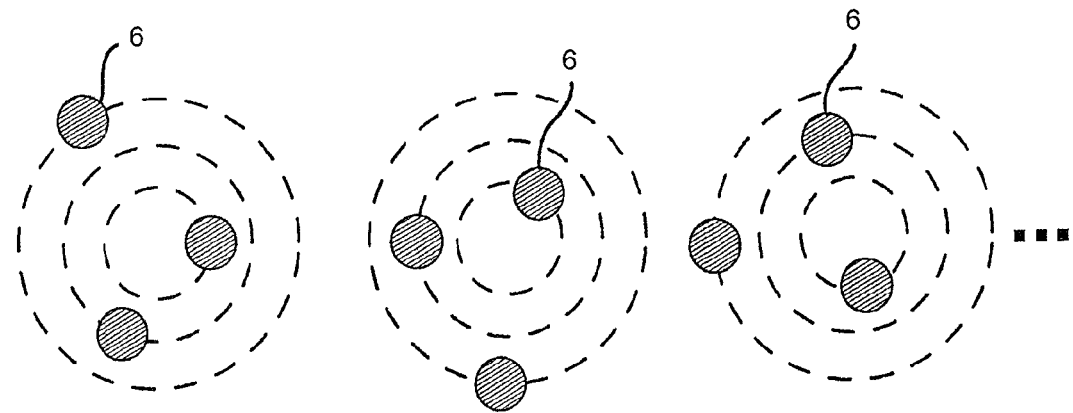
FIG. 2a shows a sequence of individual raw-data images in each of which an active subset of markers is imaged.
Figure 2B:
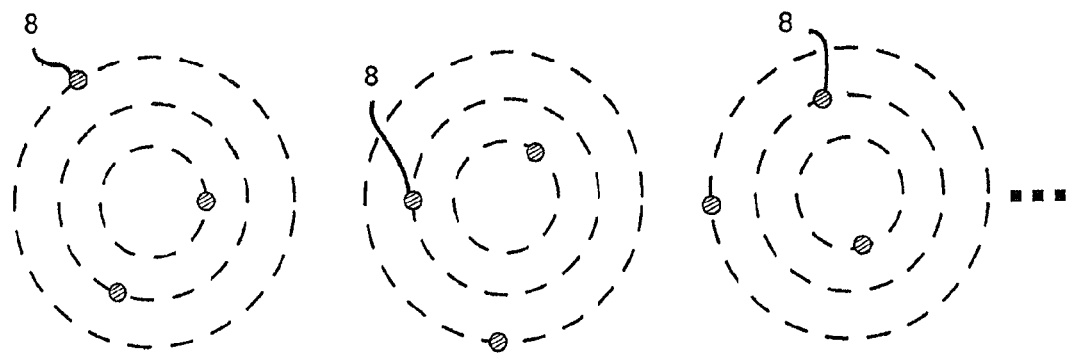
FIG. 2b shows a sequence corresponding to the image sequence of FIG. 2a, with center point positions identified from the individual raw-data images.
Figure 2C:
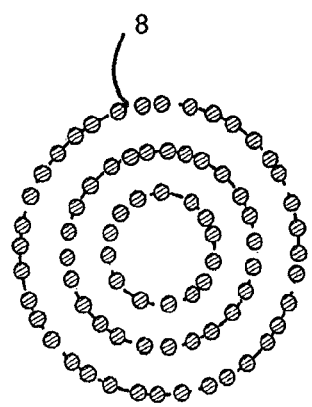
FIG. 2c is a high-resolution overall image in which the center point positions shown in FIG. 2b are combined.
Figures 3A, 3B:
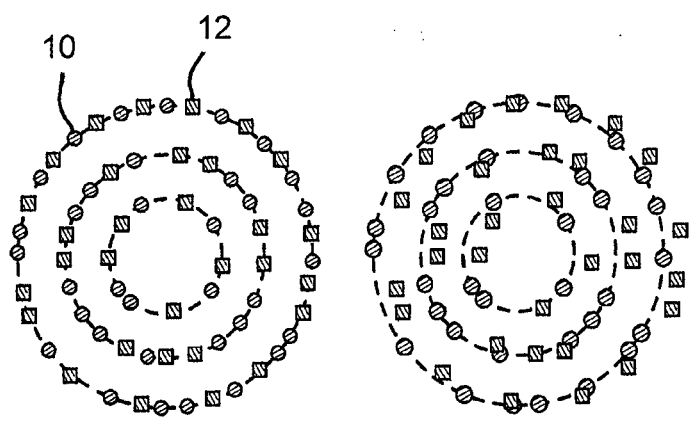
FIG. 3a is a drift-free overall image of the sample structure according to FIG. 1a, in which center point positions from two successive individual raw-data images are combined for illustrative purposes.
FIG. 3b is a drift-affected overall image of the sample structure according to FIG. 1a, in which, in accordance with FIG. 3a, center point positions of two successive individual raw-data images are combined.
Figure 4:
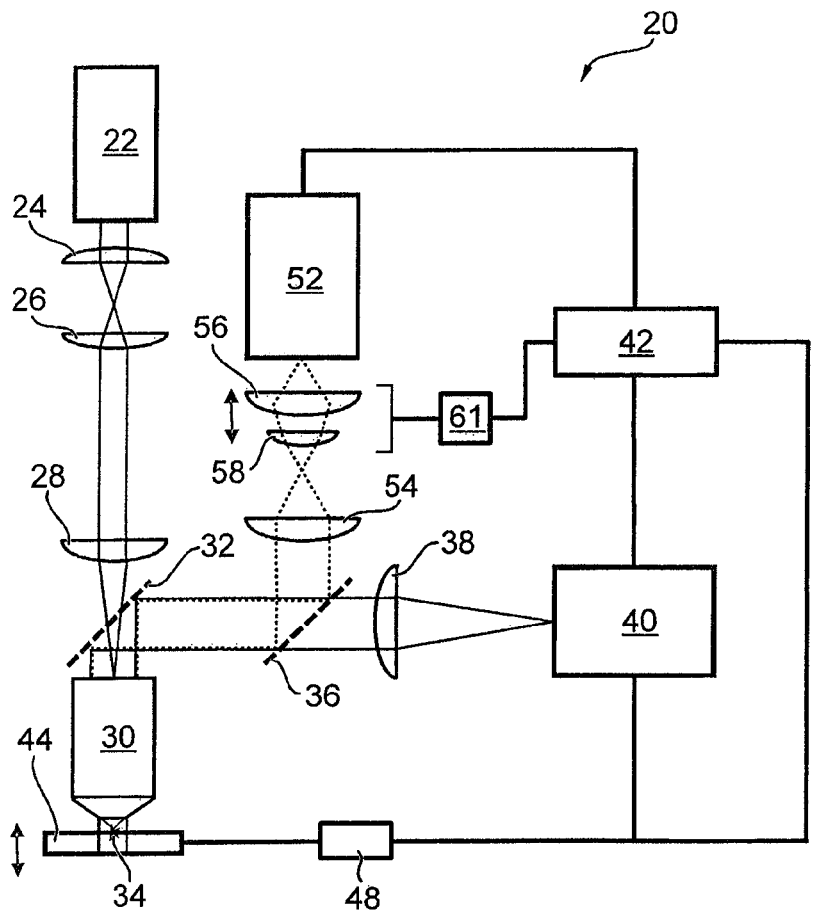
FIG. 4 shows the schematic construction of a fluorescence microscope embodied according to the present invention, as a first exemplifying embodiment.

FIG. 4 depicts a fluorescence microscope 20 that constitutes a first exemplifying embodiment of the device according to the present invention. Fluorescence microscope 20 has a light source 22 that emits excitation light onto a lens system constituted from two lenses 24 and 26. This lens system serves to collimate in the desired manner the excitation light emitted from light source 22. The collimated excitation light is then incident onto a converging lens 28 that focuses the excitation light into the aperture of an objective 30. The excitation light passes firstly through a first dichroic mirror 32 that is transparent to the excitation light. Because the excitation light emitted from light source 22 is focused into the aperture of objective 30, it emerges from objective 30 as a collimated ray bundle, and thus results in comparatively large-area, homogeneous illumination of a sample structure that is indicated in FIG. 1 by the symbol labeled 34.

As explained previously, in the present exemplifying embodiment sample structure 34 is prepared with markers, e.g. fluorescent molecules. The methods recited previously can be utilized to transfer a respective portion of these markers into the bright state, and thereby generate an active subset that is imaged in an individual image.

The fluorescent light emitted from sample structure 34 passes through objective 30 and is incident onto dichroic mirror 32. Dichroic mirror 32 is embodied so that it reflects the light emitted from sample structure 34, and thus directs it onto a second dichroic mirror 36. The latter is in turn embodied so that it allows the fluorescent light to pass, so that the fluorescent light is incident onto a lens 38 that concentrates the fluorescent light onto a light detector 40, e.g. a CCD camera. A individual image of sample structure 34 is thus generated on light detector 40. Light detector 40 converts the received fluorescent light into electrical signals, and outputs the latter to a calculation/control unit 42 in which the signals are further processed.

Figure 5:
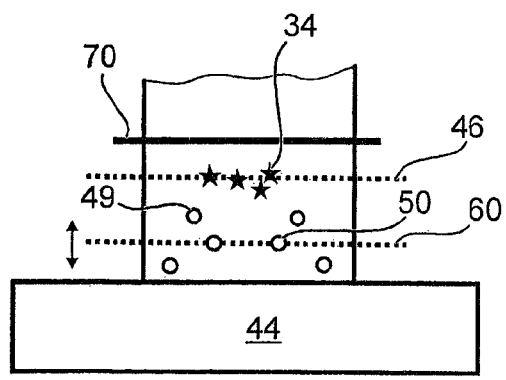
FIG. 5 shows a portion of FIG. 4 that depicts a sample structure in a first sharpness plane and a reference structure in a second sharpness plane of the optic.

Sample structure 34 is part of a sample (not further depicted in FIGS. 4 and 5) that is mounted on a sample holder 44. As shown in FIG. 5, during light-microscopy imaging sample structure 34 is located in a sharpness plane 46 of objective 30, hereinafter referred to as the "first sharpness plane." In order to allow sample structure 34 to be brought into first sharpness plane 46, sample holder 44 is vertically movable as indicated in FIG. 4 by the double arrow. Provided for this purpose is a focusing drive 48, coupled to sample holder 44, to which control is applied by calculation/control unit 42.

As is evident from FIG. 5, the sample contains not only sample structure 34 but also reference markers 49 which make possible optical sensing of a drift that occurs during acquisition of a sequence of individual images between the imaging optic, in particular objective 30, and sample structure 34. A portion of these reference markers 49 is used as reference structure 50. Fluorescence microscope 20 comprises for this purpose, in addition to the optical components recited previously (in particular, in addition to objective 30), a sub-optic described in further detail below.

This sub-optic is located in a secondary beam path that is diverted by dichroic mirror 36 from a main beam path that is defined by the light path, leading from sample structure 34 to first light detector 40, of the fluorescent light emitted from sample structure 34. The secondary beam path is directed onto a second light detector 52, e.g. a CCD camera. Located between second dichroic mirror 36 and second light detector 52 is the aforesaid sub-optic, which is made up of a stationary lens 54 and two lenses 56 and 58 displaceable relative to one another, and which of itself constitutes a lens system of variable focal length.

In the present exemplifying embodiment, autofluorescent particles or structures that are introduced into the sample, or are in any case present therein, are used as reference markers 49. What is essential is that these reference markers 49 do not need to be located in first sharpness plane 46 in which sample structure 34 is imaged. Instead, the sub-optic constituted by lenses 54 to 58 defines, in coaction with objective 30, a second sharpness plane 60 that can be shifted as desired (in FIG. 5, upward and downward) by shifting lenses 56 and 58. This makes it possible to displace second sharpness plane 60 within the sample into a region in which enough reference markers 49 that can be used as reference structure 50 imageable by light microscopy are present.

Reference structure 50 constituted by reference markers 49 arranged in second sharpness plane 60 is imaged by objective 30 and by lenses 54 to 58 onto second light detector 52. An individual image of reference structure 50 is thus generated on second light detector 52 and converted into electrical signals. These electrical signals are then conveyed to calculation/control unit 42 for evaluation. In calculation/control unit 42, changes in the position of the individual reference structure images are sensed and drift compensation values are determined therefrom, said values being used in the present exemplifying embodiment to perform a drift compensation after measurement on the sequence of individual sample structure images.

Lenses 54 and 56 of the sub-optic, which are moved with respect to one another in order to adjust second sharpness plane 60, are in this exemplifying embodiment coupled to an autofocus apparatus that automatically tracks second sharpness plane 60 when sample holder 44 is moved by means of focusing drive 48. The autofocus apparatus is constituted from calculation/control unit 42 and a drive 61 to which control is applied by calculation/control unit 42 and which moves lenses 54 and 56 in order to track second sharpness plane 60.

In the exemplifying embodiment described here, reference structure 50 constituted from a portion of reference markers 49 is generated on the basis of the autofluorescence light that is emitted from the autofluorescing reference structure 50. First dichroic mirror 32 is accordingly embodied in such a way that on the one hand it allows the excitation light emitted from laser light source 22 to pass, and on the other hand it reflects the fluorescent light emitted from sample structure 34 and the autofluorescence light emitted from the reference structure. Second dichroic mirror 36 is embodied so that it allows the fluorescent light emitted from sample structure 34 to pass, and reflects the autofluorescence light emitted from the reference structure.

This embodiment is, however, to be understood as merely an example. For example, it is also possible to image reference structure 50 using the excitation light itself. In this case, for example, reflective gold microspheres that are introduced into the sample can be used as reference markers 50.

This embodiment on the one hand makes use of the circumstance that the intensity of the excitation light emitted from laser light source 22 is as a rule comparatively high (at least in relation to the intensity of the fluorescent light emitted from sample structure 34). On the other hand, it is almost impossible in practice to achieve a transmittance of exactly 100% for first dichroic mirror 32. Instead, a small portion of the excitation light backscattered at the sample into objective 30 is always reflected at first dichroic mirror 32. If second dichroic mirror 36 is then embodied so that it allows fluorescent light to pass and reflects the excitation light, that portion of the excitation light which is inevitably reflected by first dichroic mirror 32 can be used to image reference structure 50.

Figure 6:
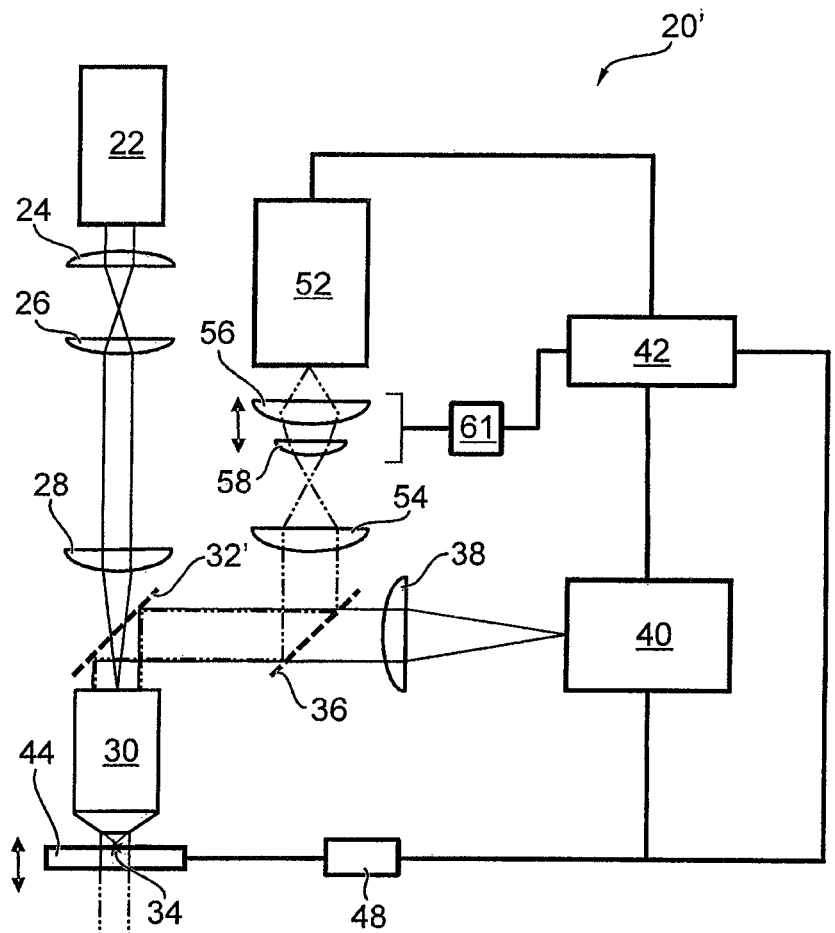
FIG. 6 shows the schematic construction of a fluorescence microscope embodied according to the present invention, as a second exemplifying embodiment.
Figure 7:
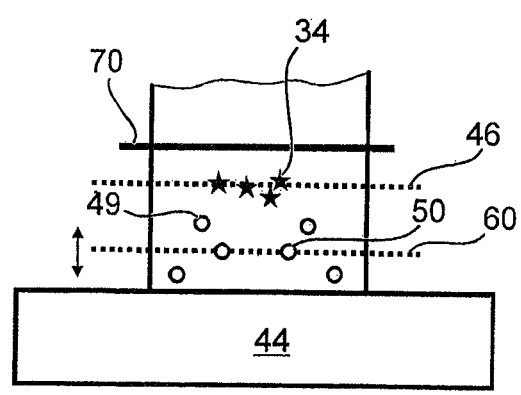
FIG. 7 shows a portion of FIG. 6 that depicts the sample structure in the first sharpness plane and the reference structure in the second sharpness plane of the optic.

FIGS. 6 and 7 show a second exemplifying embodiment of the device according to the present invention.

Whereas in the first exemplifying embodiment reference structure 50 is illuminated using the incident light method, in the second exemplifying embodiment according to FIGS. 6 and 7 a transmitted light illumination is provided. Those components of the second exemplifying embodiment which are identical to those of the first exemplifying embodiment are labeled in FIGS. 6 and 7 with the reference characters utilized in the first exemplifying embodiment. They are not described again below.

As compared with fluorescence microscope 20 according to the first exemplifying embodiment, fluorescence microscope 20' according to the second exemplifying embodiment additionally has a light source 62 as well as a lens system constituted from two lenses 64 and 66. This lens system collimates the illumination light emitted from light source 62 and directs it, from the side facing away from objective 30, onto the sample. The (in this example, transparent) sample is thus transilluminated from below in FIG. 6, so that reference structure 50 is imaged onto second light detector 52 in accordance with a usual transmitted light method, e.g. a phase contrast method.

The wavelength of the illumination light emitted from light source 62 can be selected appropriately as a function of the type of reference structure 50 to be imaged. For example, gold microspheres that are imaged in transmitted light onto second light detector 52 can be used as reference markers 49. The two dichroic mirrors 32' and 36' are modified in accordance with the selected wavelength of the illumination light emitted from light source 62, namely in such a way that they respectively reflect the illumination light of light source 62.

The exemplifying embodiments described above serve merely to explain the invention, which is not limited to those exemplifying embodiments.

The reference structure that is to be imaged can thus be embodied on coverslip 70 shown in FIGS. 5 and 7, which is part of sample holder 44. In this case second sharpness plane 60 is directed onto coverslip 70. In this case as well, the autofocus apparatus can ensure that second sharpness plane 60 is tracked so that it stays positioned on coverslip 70.

The exemplifying embodiments described above can also be modified so that drift compensation is not performed ex post facto on the individual sample structure images that have been generated, but instead during measurement, a component of fluorescence microscope 20 or 20', preferably its sample holder 44, is shifted as a function of the drift that is sensed. This can occur, for example, by appropriate application of control to focusing drive 48.

PARTS LIST 20, 20' Fluorescence microscope
22 Laser light source
24, 26 Lenses
28 Converging lens
30 Objective
32, 32' First dichroic mirror
34 Sample structure
36, 36' Second dichroic mirror
38 Lens
40 First light detector
42 Calculation/control unit
44 Sample holder
46 First sharpness plane
48 Positioning member
49 Reference marker
50 Reference structure
52 Second light detector
54, 56, 58 Lenses
60 Second sharpness plane
61 Drive
62 Light source
64, 66 Lenses

The invention claimed is:

1. A localization microscopy device for acquiring a microscopic image of a sample structure based on calculated localizations of the sample structure, said device comprising:
   an optic for imaging the sample structure and a reference structure,
   a drift sensing unit for sensing a lateral and axial drift of the sample structure relative to the optic on the basis of the imaged reference structure,
   wherein the optic comprises a first sharpness plane for imaging the sample structure and at the same time a second sharpness plane, modifiable in location relative to the first sharpness plane, for imaging the reference structure,
      wherein the optic comprises an objective for imaging the sample structure, and a sub-optic that co-acts with the objective in order to image the reference structure and is adjustable in order to modify the location of the second sharpness plane,
   and a calculation unit configured to calculate the localizations of the sample structure and to correct them on basis of the sensed lateral and axial drift.

2. The device according to claim 1, wherein the sub-optic encompasses at least two lenses movable relative to one another.

3. The device according to claim 1, wherein the sub-optic is arranged in a secondary beam path that is diverted from a main beam path intended for imaging of the sample structure.

4. The device according to claim 3, comprising a first light detector arranged in a main beam path onto which the sample structure is imageable, and a second light detector, arranged in the secondary beam path, onto which the reference structure is imageable.

5. The device according to claim 3, comprising a light-separating optical element with which the secondary beam path is diverted from the main beam path and directed onto the second light detector.

6. The device according to claim 1, wherein a light source illuminates the sample structure and at the same time the reference structure through the objective.

* * * * *